United States Patent
Pan et al.

(10) Patent No.: US 9,829,463 B2
(45) Date of Patent: Nov. 28, 2017

(54) METHOD FOR PRODUCING OXYGEN SENSOR

(71) Applicants: Wei Pan, Beijing (CN); Bin Li, Beijing (CN); Yanyi Liu, Beijing (CN); Masashi Kawai, Miyoshi (JP)

(72) Inventors: Wei Pan, Beijing (CN); Bin Li, Beijing (CN); Yanyi Liu, Beijing (CN); Masashi Kawai, Miyoshi (JP)

(73) Assignees: Toyota Jidosha Kabushiki Kaisha, Toyota-shi, Aichi-ken (JP); Tsinghua University, Beijing (CN)

(*) Notice: Subject to any disclaimer, the term of this patent is extended or adjusted under 35 U.S.C. 154(b) by 0 days.

(21) Appl. No.: 15/384,485

(22) Filed: Dec. 20, 2016

(65) Prior Publication Data
US 2017/0160225 A1    Jun. 8, 2017

Related U.S. Application Data

(62) Division of application No. 14/641,129, filed on Mar. 6, 2015, now Pat. No. 9,564,653, which is a division
(Continued)

(30) Foreign Application Priority Data

Mar. 31, 2010    (WO) .............. PCT/CN2010/071488

(51) Int. Cl.
*G01N 27/407*    (2006.01)
*G01N 33/00*    (2006.01)
(Continued)

(52) U.S. Cl.
CPC ......... *G01N 27/4073* (2013.01); *C01B 13/14* (2013.01); *C01F 17/0018* (2013.01);
(Continued)

(58) Field of Classification Search
CPC ............ H01M 8/1072; H01M 8/1093; H01M 8/1081; H01M 2250/20;
(Continued)

(56) References Cited

U.S. PATENT DOCUMENTS 5,665,482 A    9/1997    Mori et al.
2010/0028674 A1    2/2010    Ochanda
(Continued)

FOREIGN PATENT DOCUMENTS

CN    1462725 A    12/2003
CN    1840480 A    10/2006
(Continued)

OTHER PUBLICATIONS

Jones, Alison, and M. Saiful Islam. "Atomic-scale insight into LaFeO3 Perovskite: defect nanoclusters and ion migration". Journal of Physical Chemistry C 112.12 (2008): 4455-4462.*
(Continued)

*Primary Examiner* — Richard M Rump
(74) *Attorney, Agent, or Firm* — Finnegan, Henderson, Farabow, Garrett & Dunner, LLP

(57) ABSTRACT

A production method for producing an oxygen sensor, includes spinning a precursor consisting of a salt of at least one metal chosen from Sc, Y, La, Ce, Pr, Nd, Sm, Gd, Dy, Ho, Yb, Sr, Ba, Mn, Co, Mg, and Ga, a solvent, and a macromolecular polymer to produce nanofibers of the precursor containing the salt of the metal. The method further includes calcining the nanofibers of the precursor at a temperature ranging from 550° C. to 650° C. for 2 to 4 hours, and making a solid electrolyte material composed of the nanofibers obtained from the calcining. The resulting solid electrolyte material constitutes a part of the oxygen sensor.

6 Claims, 6 Drawing Sheets

Related U.S. Application Data of application No. 13/638,166, filed as application No. PCT/CN2011/072249 on Mar. 29, 2011, now abandoned.

(51) Int. Cl.

| | | |
|---|---|---|
| C01F 17/00 | (2006.01) | |
| C04B 35/48 | (2006.01) | |
| C04B 35/622 | (2006.01) | |
| C04B 35/626 | (2006.01) | |
| C04B 35/634 | (2006.01) | |
| C04B 35/64 | (2006.01) | |
| D01D 5/00 | (2006.01) | |
| D01F 9/10 | (2006.01) | |
| D01F 6/14 | (2006.01) | |
| H01M 8/1253 | (2016.01) | |
| H01M 8/126 | (2016.01) | |
| C01G 25/00 | (2006.01) | |
| C01B 13/14 | (2006.01) | |
| C01G 1/02 | (2006.01) | |
| H01M 8/124 | (2016.01) | |

(52) U.S. Cl.
CPC .......... *C01F 17/0043* (2013.01); *C01G 1/02* (2013.01); *C01G 25/00* (2013.01); *C04B 35/48* (2013.01); *C04B 35/6225* (2013.01); *C04B 35/6264* (2013.01); *C04B 35/63416* (2013.01); *C04B 35/64* (2013.01); *D01D 5/0015* (2013.01); *D01F 6/14* (2013.01); *D01F 9/10* (2013.01); *G01N 33/0036* (2013.01); *H01M 8/126* (2013.01); *H01M 8/1253* (2013.01); *C01P 2002/72* (2013.01); *C01P 2004/04* (2013.01); *C01P 2004/10* (2013.01); *C01P 2004/16* (2013.01); *C01P 2004/17* (2013.01); *C01P 2006/40* (2013.01); *C04B 2235/3224* (2013.01); *C04B 2235/3225* (2013.01); *C04B 2235/3229* (2013.01); *C04B 2235/3248* (2013.01); *C04B 2235/522* (2013.01); *C04B 2235/5236* (2013.01); *C04B 2235/656* (2013.01); *C04B 2235/6567* (2013.01); *C04B 2235/96* (2013.01); *H01M 2008/1293* (2013.01); *H01M 2250/30* (2013.01)

(58) Field of Classification Search
CPC ........ H01M 2300/0071; H01M 8/1246; B82Y 30/00; D01F 9/10; D01F 6/14; C04B 35/63416; C04B 35/62231; C04B 35/6225; D01D 5/0015; C01G 25/02; C01F 17/0043; Y02T 90/32; Y02P 70/56; Y02E 60/525

See application file for complete search history.

(56) References Cited

U.S. PATENT DOCUMENTS

| 2010/0167078 A1 | 7/2010 | Kim et al. |
| 2011/0052467 A1 | 3/2011 | Chase et al. |
| 2013/0089485 A1 | 4/2013 | Pan et al. |

FOREIGN PATENT DOCUMENTS

| CN | 101235556 A | 8/2008 |
| CN | 101362649 A | 2/2009 |
| CN | 101624205 A | 1/2010 |
| CN | 101805942 A | 8/2010 |
| CN | 101850245 A | 10/2010 |
| CN | 101899725 A | 12/2010 |
| JP | 59-18271 | 1/1984 |
| JP | 9-2873 | 1/1997 |
| JP | 2000-109318 | 4/2000 |
| JP | 2004-87271 | 3/2004 |
| JP | 2004-143023 | 5/2004 |
| JP | 2004-339035 | 12/2004 |
| JP | 2006-244810 | 9/2006 |
| JP | 2007-290909 A | 11/2007 |
| JP | 2009-197351 | 9/2009 |
| JP | 2009-235629 | 10/2009 |
| WO | WO 2009/117114 A | 9/2009 |

OTHER PUBLICATIONS

Hong-Wei, Ji, et al. "Fabrication of LaFeO3 Micro-nanofiber by Electrospinning." Chemical Journal of Chinese Universities-Chinese 30.11 (2009): 2112-2115. (Translation).*

X. Yang, "Fabrication of One-dimensional Metal Oxide Nanomaterials by Electrospinning," Master Thesis of Northeast Normal University, pp. 28-37 (Jul. 7, 2005).

Y. Li et al., "Electrospinning Preparation and Magnetic Properties of $Mn_2O_3$ Nanofibers," Chemical Journal of Chinese Universities, vol. 31, No. 1, pp. 16-19 (Jan. 2010).

Y. Liu et al., "Fabrication of MgO Nanofibers by Electrospinning," Journal of Molecular Science, vol. 20, No. 2, pp. 54-57 (Jun. 2004).

H. Guan et al., "Fabrication of $ZrO_2$ Nanofibers by Electrospinning," Chemical Journal of Chinese Universities, vol. 25, No. 8, pp. 1413-1415 (Aug. 2004).

L. Liu et al., "Preparation and Characterization of $Y_2O_3$ Nanofibers via Electrospinning," Journal of the Chinese Rare Earth Society, vol. 26, No. 4, pp. 400-404 (Aug. 2008).

Shao, Changlu et al., "A novel method for making $ZrO_2$ nanofibres via an electrospinning technique," Journal of Crystal Growth 267, (2004), pp. 380-384.

Guan, Hongyu et al., A novel method for preparing $Co_3O_4$ nanofibers by using electrospun PVA/cobalt acetate composite fibers as precursor, Materials Chemistry and Physics 82, (2003), pp. 1002-1006.

Li, Dan et al., "Electrospinning: A Simple and Versatile Technique for Producing Ceramic Nanofibers and Nanotubes," J. Am. Ceram. Soc., 89(6), (2006), pp. 1861-1869.

Azad, Abdul-Majeed, "Fabrication of yttria-stabilized zirconia nanofibers by electrospinning," Materials Letters 60, (2006), pp. 67-72.

Yang, Xinghua et al., "Nanofibers of $CeO_2$ via an electrospinning technique," Thin Solid Films 478, (2005), pp. 228-231.

Yu, Na et al., "Nanofibers of $LiMn_2O_4$ by electrospinning," Journal of Colloid and Interface Science 285, (2005), pp. 163-166.

Fu, Zheng-Wen et al., "Nanostructured $LiCoO_2$ and $LiMn_2O_4$ fibers fabricated by a high frequency electrospinning," Solid State Ionics 176, (2005), pp. 1635-1640.

Dharmaraj, N. et al., "Preparation and morphology of magnesium titanate L anofibers via electrospinning," Inorganic Chemistry Communications 7, (2004), pp. 431-433.

Shao, Changlu et al., "Preparation of $Mn_2O_3$ and $Mn_3O_4$ nanofibers via an electrospinning technique," Journal of Solid State Chemistry 177, (2004), pp. 2628-2631.

Azad, Abdul-Majeed Azad, "Processing and characterization of electrospun $Y_2O_3$-stabilized $ZrO_2$ (YSZ) and $Gd_2O_3$-doped $CeO_2$ (GDC) nanofibers," Materials Science and Engineering B 123, (2005), pp. 252-258.

J. Zhan et al., "Bulk Synthesis of Single-Crystalline Magnesium Oxide Nanotubes," *Inorg. Chem.*, 2004, 43 (8) 2462-2464.

Wang, H. et al., "The Preparation Progresses of YSZ Nanometer Powder," Bulletin of the Chinese Ceramic Society, vol. 25, No. 6, Dec. 2006, pp. 117-122.

Hong-Wei, J. et al., "Fabrication of $LaFeO_3$, Micro-nanofiber by Electrospinning," Chemical Journal of Chinese Universities, vol. 30, No. 11, Nov. 2009, pp. 2112-2115.

Zhou, B., "Preparation and Characterization of Rare Earth Fluoride Nanofiber by Electrospinning, Technology," available from Chinese Master's Thesis Full-Text Database, Engineering Technology I, published from Dec. 16, 2008 to Jan. 15, 2009, No. 1B016-48.

Office Action in U.S. Appl. No. 13/638,166, dated Apr. 3, 2013.

(56) References Cited

OTHER PUBLICATIONS

Office Action in U.S. Appl. No. 13/638,166, dated May 9, 2013.
Office Action in U.S. Appl. No. 13/638,166, dated Oct. 21, 2013.
Office Action in U.S. Appl. No. 13/638,166, dated Mar. 13, 2014.
Advisory Action in U.S. Appl. No. 13/638,166, dated Jun. 13, 2014.
Office Action in U.S. Appl. No. 13/638,166, dated Jul. 16, 2014.
Office Action in U.S. Appl. No. 13/638,166, dated Nov. 7, 2014.
Jones, A. et al., Atomic-Scale Insight into $LaFeO_3$ Perovskite: Defect Nanoclusters and Ion Migration, Journal of Physical Chemistry C, vol. 112, No. 12 (2008), pp. 4455-4462.
Office Action in U.S. Appl. No. 14/641,129, dated Nov. 12, 2015.
Notice of Allowance and Notice of Allowability in in U.S. Appl. No. 14/641,129, dated Sep. 22, 2016.

* cited by examiner

METHOD FOR PRODUCING OXYGEN SENSOR

CROSS-REFERENCE TO RELATED APPLICATIONS

This is a division of application Ser. No. 14/641,129, which is a division of application Ser. No. 13/638,166, which is a national phase application of International Application No. PCT/CN2011/072249, filed Mar. 29, 2011, and claims priority of International Application No. PCT/CN2010/071488, filed Mar. 31, 2010, the content of each of which is incorporated herein by reference.

FIELD OF THE INVENTION

The present invention relates to a solid electrolyte material and a production method therefor, particularly relates to a high ion conductive or an ion/electron mix conductive electrolyte material and production method therefor.

BACKGROUND ART

Theoretically, a fuel cell outputs electric power along with water generated by reaction of oxygen and hydrogen only, thus it is a clean energy source without being a burden on the environment. The electrolyte materials used in fuel cell mainly include: polymer solid electrolyte type fuel cell ("PEFC" for short), phosphoric acid fuel cell ("PAFC" for short), molten carbonate fuel cell ("MCFC" for short), solid oxide fuel cell ("SOFC" for short), and the like. Among them, SOFC uses an ion conductive metal oxide as the electrolyte, and uses a mix conductive oxide as (cathode) the air electrode.

Solid electrolyte material is a key material used in the applications such as fuel cell and oxygen sensor and the like in the fields like automobile. At present, mature solid electrolyte materials in the world include oxide materials like yttrium-stabilized zirconia ("YSZ" for short) and the like, which are used for fuel cell, oxygen sensor, and etc. Such materials, with a operation temperature of usually about 1000° C., have excellent performances and a relatively lower price. However, the high operation temperature of 1000° C. causes difficulty in manufacturing and operating devices, whilst the chemical reaction between YSZ and member materials also results in deterioration of materials due to long-term use under high temperature, and makes it difficult to perform processes like material joining, etc. On the other hand, electrolyte materials used for automobile exhaust gas sensors need to overcome problems such as thermal shock failure, long start-up time, etc. In recent years, countries in the world have paid attention to the development of materials which have high ionic conductivity at low temperatures. Particularly, for devices with high power output at a relatively low temperature, solid electrolyte materials are required to have high ionic conductivity and high stability at low temperatures. Besides, electrode materials for the air side of a fuel cell demand for oxide materials with high mix conductivity.

So far, solid electrolyte materials developed and disclosed include lanthanum gallate oxides series (Patent Literature 1), a mixed system of stable bismuth oxide series and stable zirconia (Patent Literature 2) and cerium oxide series composite oxides (Patent Literatures 3-6).

Cerium oxide ($CeO_2$), zirconia, bismuth oxide and the like are all ion conductive materials with fluorite structure. High oxygen-ion conductivity is obtained by doping with low-valence metal elements to form oxygen deficiency (vacancy). For example, Patent Literature 3 teaches to further dope cerium oxide with other 1-valence or 2-valence elements on the basis of doping it with 3-valence rare earth element, such as doping cerium oxide with yttrium oxide. In Patent Literature 4, a high ionic conductivity is obtained by partly replacing cerium atoms in cerium oxide with lanthanum atoms of large ion radius, and replacing cerium atoms with strontium (Sr) or barium (Ba) of 2-valence to increase disorder in the oxygen vacancy. Patent Literature 5 teaches that replacing the position of 4-valence cerium with greater cations of 2-valence and 3-valence results in oxygen deficiency, and in a greater crystallization stress, and a high ionic conductivity is thus obtained. Patent Literature 6 teaches a high oxygen-ion conductivity at a temperature of 800° C. or lower and an oxygen partial pressure of 10-30-10-15 atmospheric pressure (atm) is obtained by doping cerium oxide with elements such as ytterbium (Yb), yttrium (Y), gadolinium (Gd), samarium (Sm), neodymium (Nd), Lanthanum (La) and the like.

However, in case that a metal oxide is used as the cathode and the electrolyte material of fuel cells (SOFC), chemical reactions between three phase materials of gas/electrode/electrolyte often occur, in which gas, ion and electron participate simultaneously. To facilitate the above reactions, solid electrolyte and electrode having fibrous metal oxide have been invented, as shown in Patent Literatures 7 and 8.

When the cerium oxide series composite oxides as described in Patent Literatures 3-5 are doped with alkaline earth metals, carbonates are easily generated under the effect of ambient atmosphere, which results in a decrease in conductivity, and in turn arouses the problem of structural stability of the solid electrolyte materials during usage. In general, addition of 3-valence rare earth elements or 2-valence alkaline earth metal elements into oxides of 4-valence cerium can all increase the concentration of oxygen vacancy, but excessive doping may lead to generation of other compounds, and thus cause a decrease in conductivity. Furthermore, 4-valence cerium ion $Ce^{4+}$ in cerium oxide will be reduced to 3-valence cerium ion $Ce^{3+}$ at a high temperature and a reducing atmosphere to give rise to electronic conductivity, and thereby reduce ionic conductivity and the efficiency of fuel cells. Besides, the reduction reaction also leads to crack of the cerium oxide solid electrolyte material, and thus failure.

Hence, although various composite oxide solid electrolyte materials have been developed up to the present, demands for fuel cells (SOFC) with high ionic conductivity and high power output under low operation temperature can still hardly be met.

Patent Literature 1: Japanese Publication JP2004-339035;
Patent Literature 2: Japanese Patent JP59-18271;
Patent Literature 3: Japanese Patent JP09-2873;
Patent Literature 4: Japanese Patent JP2000-109318;
Patent Literature 5: Japanese Patent JP2004-87271;
Patent Literature 6: Japanese Patent JP2004-143023;
Patent Literature 7: Japanese Patent JP2006-244810;
Patent Literature 8: Japanese Patent JP2009-197351.

SUMMARY OF THE INVENTION

In view of the above, an object of the present invention is to provide nanofibers of metal oxide, which has high ionic conductivity at low temperature.

Moreover, another object of the present invention is to provide a solid electrolyte and/or fuel cell formed from said metal oxide, where the solid electrolyte material has a high ionic conductivity and ionic/electronic mix conductivity at low temperature, and the fuel cell has a high output power at low temperature.

Furthermore, another object of the present invention is to provide a production method for nanofibers of metal oxide.

To achieve the above objects, based on the study of the prior invention patents, the inventors, targeting the above metal oxide having ionic conductivity, adopted the manufacturing technique for nanofibers, controlled grain growth by low-temperature synthesis calcination, and thereby obtained a high ion conductive solid electrolyte material with very low intragranular and intergranular impedances, said material having very high conductivity under low temperature.

To be specific, the present invention is mainly described as follows:

According to one aspect of the present invention, a production method for nanofibers of metal oxide is provided, wherein the metal oxide is a metal oxide of at least one metal selected from Sc, Y, La, Ce, Pr, Nd, Sm, Gd, Dy, Ho, Yb, Zr, Sr, Ba, Mn, Fe, Co, Mg and Ga, the method comprising:
  a) a precursor containing a salt of the above metal may be spun, to obtain nanofibers of the precursor containing the salt of the metal;
  b) the nanofibers of the precursor containing the salt of the metal may be calcined at a temperature ranging from 500° C. to 800° C., to obtain the nanofibers of metal oxide.

According to one aspect of the present invention, the metal oxide may be a metal oxide of at least one metal selected from Sc, Y, La, Ce, Pr, Nd, Sm, and Gd.

According to one aspect of the present invention, the precursor may contain a macromolecular compound.

According to one aspect of the present invention, the nanofibers of the precursor of the metal oxide may be produced by means of electrospinning or liquid phase spinning.

According to another aspect of the present invention, nanofibers of metal oxide are provided, wherein the metal oxide is a metal oxide of at least one metal element selected from Sc, Y, La, Ce, Pr, Nd, Sm, Gd, Dy, Ho, Yb, Zr, Sr, Ba, Mn, Fe, Co, Mg and Ga, wherein, the average diameter of the nanofibers may range from 20 to 1000 nm, the average grain size of the crystals in the nanofibers may range from 2 to 20 nm.

According to one aspect of the present invention, a solid electrolyte material is provided, which may contain the above nanofibers of metal oxide.

According to one aspect of the present invention, a fuel cell is provided, which may be produced from the above solid electrolyte material.

According to one aspect of the present invention, an oxygen sensor is provided, which may be produced from the above solid electrolyte material.

The solid electrolytic nanofibers of cerium oxide series manufactured according to the present invention can significantly reduce intragranular and intergranular resistance of the material. Meanwhile, the material is characterized in high oxygen ion conductivity or oxygen ion/electron and hole mix conductivity. Compared with the traditional bulk materials or film materials, it has a significantly high ionic or mix conductivity, thus can be used as a novel solid electrolyte material of high ionic conductivity or mix conductivity.

BRIEF DESCRIPTION OF THE DRAWINGS

The above and/or additional aspects and advantages of the invention will become more apparent and easy to understand from the following description of the preferred embodiments taken in conjunction with accompanying drawings, wherein:

FIGS. 2(a), 2(b), and 2(c) show schematic diagrams of an apparatus for testing electrical properties of one-dimensional nanofibers of a nano metal oxide, wherein FIG. 2(a) is a schematic diagram of fabrication of the one-dimensional nanofibers; FIG. 2(b) is a schematic diagram of nanofibers in an oriented alignment on a quartz crystal plate; FIG. 2(c) is a schematic diagram of the apparatus for testing electrical properties of the orientedly aligned nanofibers.

FIGS. 3(a) and 3(b) show photos of nanofibers of gadolinium-doped cerium oxide ("GDC" for short) according to an Example of the present invention observed under a field emission scanning electron microscope ("FESEM" for short), wherein FIG. 3(a) is a photo of the initially formed GDC/polyvinyl alcohol composite nanofibers observed under a FESEM; FIG. 3(b) is a FESEM image of the GDC nanofibers after calcination under 500° C.

FIGS. 5(a), 5(b), and 5(c) show high-resolution transmission electron microscope (HRTEM) images of the GDC nanofibers obtained by the production method according to an Example of the present invention, wherein FIG. 5(a) is a HRTEM image of the GDC nanofibers after calcining under 500° C.; FIG. 5(b) is a HRTEM image of the GDC nanofibers after calcining under 600° C.; FIG. 5(c) is a HRTEM image of the GDC nanofibers after calcination.

DESIGNATION OF SYMBOLS

Figure 1:
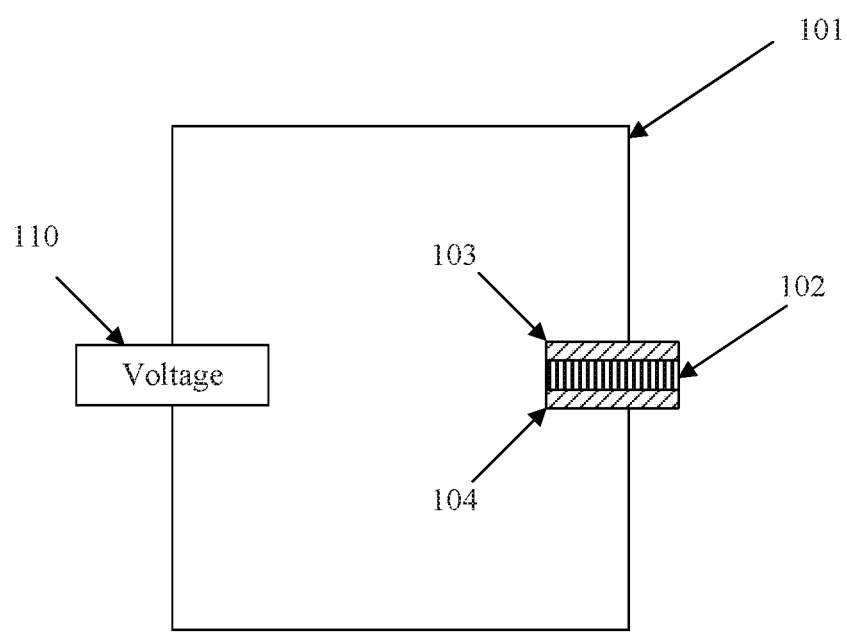
FIG. 1 shows a schematic diagram of a fuel cell consisting of nanofibers solid electrolyte of metal oxide prepared according to an Example of the present invention.

101: fuel cell
102: solid electrolyte
103: cathode
104: anode
110: external circuit

SPECIFIC MODE FOR CARRYING OUT THE INVENTION

The additional aspects and advantages will be partially set forth or made apparent in the following description, or will be learned through practices of the present invention.

I. Nanofibers of Metal Oxide

"Metal oxide" herein is intended to mean a compound with an oxide of metal element as its main form. Said metal oxide may contain one or more metal elements, preferably contain one to two metal elements. The metal element may be at least one of rare-earth metals such as scandium, yttrium, lanthanum, cerium, praseodymium, neodymium, samarium, gadolinium, dysprosium, holmium, ytterbium, etc., as well as other metals such as zirconium, strontium, barium, manganese, iron, cobalt, magnesium and gallium, etc., preferably at least one of the elements scandium, yttrium, lanthanum, cerium, praseodymium, neodymium, samarium or gadolinium. More preferably, the metal oxide contains at least one of the elements scandium, cerium, praseodymium, samarium and gadolinium. Moreover, the metal oxide may also contain other metal elements. However, metal elements of the metal oxide with the best effect in the present invention are selected from the above metals.

The present invention is not limited to particular metal oxides, such as metal oxides wherein two rare earth metal elements are contained in gadolinium-doped cerium oxide (GDC), yttrium-stabilized zirconia (YSZ), oxides with perovskite structure (such as LSGM, BSCF) or metal oxides with pyrochlore structure containing for example rare earth metal elements and other metal elements.

The method for preparing nanofibers of metal oxide by using the above mentioned metal oxide to obtain a solid electrolyte material with high ionic conductivity or mix conductivity will be described in detail as follows "Nanofibers" of the present invention is a fibrous material, with a wide range of diameters of the nanofibers. The average diameter may range from 20 to 1000 nm. The ratio of the longitudinal average length to the average diameter of the fibers is greater than 100, wherein the average diameter is preferably in the range of from 40 to 500 nm, and more preferably in the range of from 50 to 100 nm. The average length of the above nanofibers is preferably 100000 times, and more preferably 1000000 times of the average diameter. In other words, the average length is preferably greater than 0.4 cm, and more preferably greater than 5 cm.

The average length and the average diameter of the nanofibers are average values obtained by measuring 10 nanofibers using a scanning electron microscope (SEM) and a high-resolution transmission electron microscope (HRTEM). The average diameter of the nanofibers can also be calculated by measurement according to the method of peak width at half height by X-ray diffraction (XRD).

The nanofibers of metal oxide of the present invention are obtained by subjecting the nanofibers containing the metal salt to calcination under at high temperature. The oxide nanofibers containing at least one metal element with suitable length and average diameter can be obtained by controlling the temperature and time of calcination. The calcination process is described as follows.

"Calcination process" herein is intended to mean a process in which a salt of a metal is oxidized to form a metal oxide, the metal oxide crystallizes at a temperature lower than the melting point of the metal oxide, and small metal oxide crystals gradually aggregate and grow into bigger crystals. That is, the "calcination process" includes the process of formation of a metal oxide, crystallization of the metal oxide and growth of crystal grains. The inventive nanofibers of metal oxide are composed of metal oxide crystal with a three-dimensional structure. In the inventive nanofibers of metal oxide, adjacent metal oxide crystal grains connect to form a grain boundary network structure, and thus a higher ionic conductivity can be obtained. Herein the average grain size of the metal oxide nanofibers preferably ranges from 2 to 20 nm, more preferably from 4 to 10 nm. Under this circumstance, the density of the metal oxide nanofibers after calcination should be 90% or higher of the theoretical density, preferably 95% or higher. Solid electrolyte material with high performance can be obtained by using the nanofibers with the above mentioned performances, and can satisfy and promote miniaturization application of solid electrolyte fuel cells. The crystalline phase and the average grain size of the inventive nanofiber material can be obtained from the average taken by measuring the length along the long-axis direction of 10 or more grains by SEM and HRTEM, or can be determined by XRD measurement. The calcined density can be derived by computing according to the Archimedes method. The X-ray diffraction method is utilized to obtain lattice constant, and the theoretical density can thus be calculated based on the lattice constant.

Figure 7:
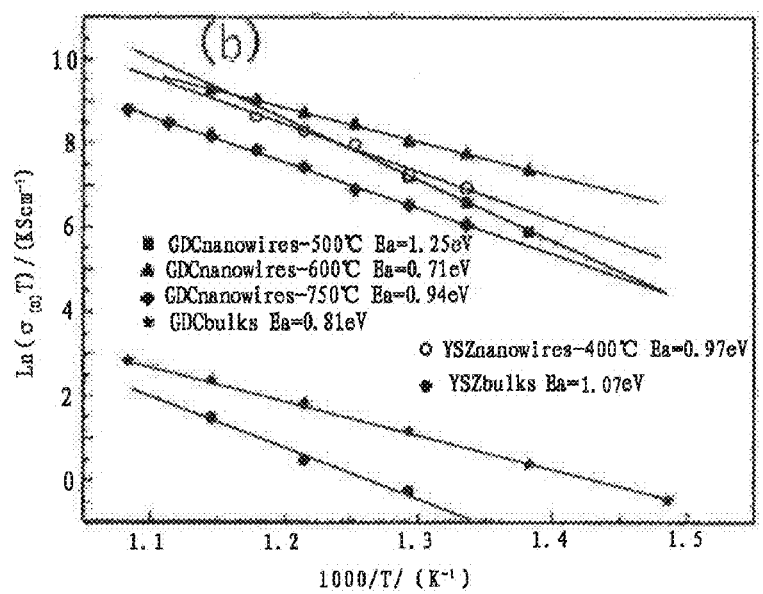
FIG. 7 shows a diagram of conductivity versus temperature of the GDC and YSZ nanofibers prepared by the production method according to an Example of the present invention.

In the present invention, "solid electrolyte" is intended to mean solid material with ionic conductivity. The above mentioned solid electrolyte of the inventive metal oxide nanofibers has a very high conductivity performance at low temperature (FIG. 7). Compared with the existing inventions, the inventive metal oxide nanofibers have a grain size smaller than that of the previous nanofibers and bulk materials, with a three-dimensional crystalline configuration (see Patent Literature 8). The grain resistance and the intergranular resistance of the inventive metal oxide nanofibers are significantly reduced. Therefore, at the operation temperature ranging from 400 to 600° C., the conductivity of the solid electrolyte of the inventive metal oxide nanofibers is 100 to 1000 times higher than that of the previous bulk metal oxide solid electrolyte with the same chemical composition. In addition, the solid electrolyte of the inventive metal oxide nanofibers has an operation temperature range several hundred degrees lower than that of the traditional solid electrolyte materials, at the same conductivity.

The above conductivity can be measured by using an equivalent circuit model, via AC Impedance Spectroscopy measuring method, and the total resistance, grain resistance and intergranular resistance are calculated by using Cole-Cole plot, and then the corresponding conductivity can be calculated.

Since the solid electrolyte of the inventive metal oxide nanofibers has a high ionic conductivity at low temperature, it may preferably be used for solid electrolyte fuel cells or oxygen sensors. FIG. 1 shows a schematic diagram of a solid electrolyte fuel cell unit comprising the inventive metal oxide nanofibers. However, the present invention is not limited hereto in terms of application of practical fuel cells. 101 in the figure is the solid electrolyte fuel cell comprising the inventive metal oxide nanofibers, which consists of solid electrolyte 102 of the inventive metal oxide nanofibers, and a pair of electrodes, i.e., cathode 103 and anode 104. Here, air is introduced at the cathode side 103, and hydrogen gas and other fuels are provided via the anode side 104, and electromotive force is generated on an external circuit load 110. The fuel cell consisting of the above nanofibers of metal oxide has excellent properties, particularly, it enables a stable power output in a low temperature region at the operation temperature of from 400 to 600° C.

II. Production Method for the Nanofibers of Metal Oxide

The production method for the inventive metal oxide nanofibers includes the preparation process of nanofibers and the calcination process. Each process is illustrated as follows.

Preparation of Nanofibers

An object of this process is to subject a precursor containing a salt of a metal to nanofiber spinning, to form nanofibers containing the salt the metal. The "precursor" herein is intended to mean a substance used for forming nanofibers containing the salt of the metal. During the formation of the nanofibers, the chemical components of the precursor include a solvent and various compounds besides the salt of the metal which is necessary for eventually forming the nanofibers of metal oxide. The precursor is generally in colloidal form. In this case, the composition of the solvent is not specifically restricted, which can be an organic solvent, or can be water or alcohol, preferably water.

The salt of the metal may be a salt of the cation of the aforementioned metal, without particular limitation on its composition. The types of salts, which vary depending on the specific cation of the metal, may be inorganic salts such as nitrate, sulfate, halide and the like, as well as organic salts containing the cations. Preferred salts in the present invention are salts containing nitrate ions. The concentration of the salt of the metal in the precursor is preferably in the range of 2 and 10 wt %, based on mass percentage.

To form nanofibers with smooth and uniform diameter, the chemical components of the precursor generally contain a macromolecular polymer, and other compounds may be contained as well. The purpose for choosing such precursor composition is to obtain a colloidal substance with a high viscosity. The macromolecular compound used in the precursor is not particularly limited, which is open to various options, for example, polyvinyl alcohol (PVA), polyvinyl butyral, polyethylene glycol, etc. Polyvinyl alcohol is preferred in the present invention. The average polymer molecular weight (Mw) preferably ranges from 1000 to 100000. The concentration of the polymer is generally 5 wt % to 15 wt %, based on mass percentage. During the formation of the precursor colloidal substance containing the salt of the metal, solvent, macromolecular compound, there is no particular limitation on the process sequence. Thus it is possible to firstly dissolve the macromolecular compound into the solvent, or firstly dissolve the salt of the metal into the solvent, or simultaneously dissolve the salt of the metal and the macromolecular compound into the solvent. Preferably, the macromolecular compound is firstly dissolved into the solvent, followed by dissolving the salt of the metal into the solvent in which the macromolecular compound has been previously dissolved. A colloidal precursor solution suitable for preparation of nanofibers can be obtained by the above method. The processes for spinning the inventive nanofibers are not particularly limited, for example, besides the electrospinning method, other methods such as sol-spinning, solution-jet weaving, or blend melt spinning of nano polymers and so on are likewise available. However, the electrospinning method is preferably adopted in the present invention. Each of those spinning methods are technologies which have been disclosed. Taking the electrospinning method as example, the precursor solution prepared by the above method is sprayed through a nozzle to a substrate, between which an electric field with certain voltage is applied, to form the nanofibers containing the salt of the metal. In this case, the diameter of the nozzle is selected to be in a range of from 0.5 to 4 mm, the voltage of the applied electric field is selected to be in a range of from 10 to 30 kV. The distance between the nozzle and the substrate is selected to be in a range of from 10 to 30 cm.

In case that the solution high-pressure spray method is employed, the precursor solution prepared by the above method is injected into a vessel with a slit, with a high pressure applied in the vessel, which forces the metal salt precursor solution to be sprayed from the slit to form fibers. In this case, preferably the width of the slit is in the range of from 0.1 to 0.5 mm, and preferably the applied pressure is in the ranges of from 1 to 10 MPa.

The nanofibers of the precursor containing the salt of the metal can thus be obtained. Next, it is possible to obtain the nanofibers of metal oxide with suitable shape and length via the calcination process as set forth below.

Calcination Process

In this process, the resultant nanofibers containing the salt of the metal from the above process are subjected to calcination to form the nanofibers in the form of metal oxide calcinate. Through this process, the metal is oxidized to form a metal oxide, followed by crystallization, aggregation of the metal oxide and growth of the crystal, the metal oxide crystal with larger grain size is thus formed. During this process, the calcining temperature ranges from 500 to 800° C., preferably from 550 to 650° C. The calcination generally lasts for 2 to 10 h or more, preferably 2 to 4 h. Although the calcination process may proceed in an air atmosphere, to accelerate the calcination, it is also possible to reduce the oxygen partial pressure in the atmosphere. For example, calcination proceeds in a hydrogen gas atmosphere, a nitrogen gas atmosphere, vacuum or a mixed atmosphere of hydrogen gas and argon gas.

In the present invention, the calcination is carried out at a temperature much lower than in the prior arts, obtaining the well crystallized metal oxide nanofibers. The low-temperature calcination results in nanofibers in which the metal oxide with nano crystal grains aligns in three-dimensional crystal. Connections between adjacent metal oxide grains in the three-dimensional crystalline alignment of the metal oxide nanofibers construct a grain boundary network structure, which eventually reduces the intergranular and intragranular impedances significantly. Therefore, the nanofibers of metal oxide with a high ionic conductivity in a low temperature region can be obtained according to the technology of the present invention.

Moreover, in case that the precursor contains a macromolecular compound, during the calcination, the macromolecular compound in the nanofibers of metal salt is removed from the nanofibers by burning. The removal of the macromolecular compound results in diameter shrinkage of the nanofibers, and the nanofibers of metal oxide with a suitable diameter are finally obtained.

The resultant high ion-conductive nanofibers of metal oxide can be used as miniature solid electrolyte material.

According to the above description, the nanofibers of metal oxide with high ion-conductivity in low temperature range can be obtained by the production method of the present invention.

Thus, the solid electrolyte of the nanofibers of metal oxide obtained according the inventive production method can be used to manufacture miniature fuel cells as the power source of cell phone, laptop or other portable electronic devices, or oxygen sensors.

The Examples described below by referring to the drawings are exemplary, which only serve to illustrate the present invention but can be construed to be restrictive.

Raw Materials:
Ce(NO$_3$)$_3$.6H$_2$O (purity: 99.9% or more);
Gd(NO$_3$)$_3$.6H$_2$O (purity: 99.9% or more);
Y(NO$_3$)$_3$.6H$_2$O (purity: 99.9% or more);
ZrO(NO$_3$)$_2$.2H$_2$O (purity: 99.9% or more);
Polyvinyl alcohol (PVA, MW=8000).

Preparation of Nanofibers of Metal Oxide

A precursor solution of Ce$_{0.9}$Gd$_{0.1}$O$_{1.95}$ (GDC) was prepared according to the following method.

0.6 g of PVA particles were dissolved in 5.4 g of deionized water, which was heated at the temperature of 60° C. while stirring for 3 h, to give a PVA aqueous solution. Thereafter, 0.48 g of metal nitrate containing cerium and gadolinium (with a mole ratio of Ce:Gd=9:1) was added into the above PVA aqueous solution. A transparent colloidal precursor solution of cerium nitrate/PVA containing gadolinium was obtained after stirring for 2 h at room temperature.

Similarly, a precursor solution of Y$_2$O$_3$—ZrO$_2$ (YSZ) of 8 mol % was prepared. A PVA aqueous solution was prepared following the same method as hereinabove. Thereafter, 0.36 g of zirconium nitrate containing yttrium (with mole ratio of Zr:Y=23:4) was added into the PVA aqueous solution. A cerium (yttrium) nitrate/PVA transparent colloidal precursor solution was obtained after stirring for 2 h at room temperature.

The resultant transparent colloidal precursor solutions were added into a syringe used for subcutaneous injection; 16 kV voltage was applied between the needle of the syringe and a substrate electrode for receiving fibers; meanwhile, the distance between the needle of the syringe and the substrate electrode for receiving fibers is set at 16 cm. Then, the nanofibers of the precursor are sprayed from the needle of the syringe, and collected onto the substrate. The apparatus for electrospinning is shown in details in FIGS. 2(a), 2(b), and 2(c).

Figure 2A:
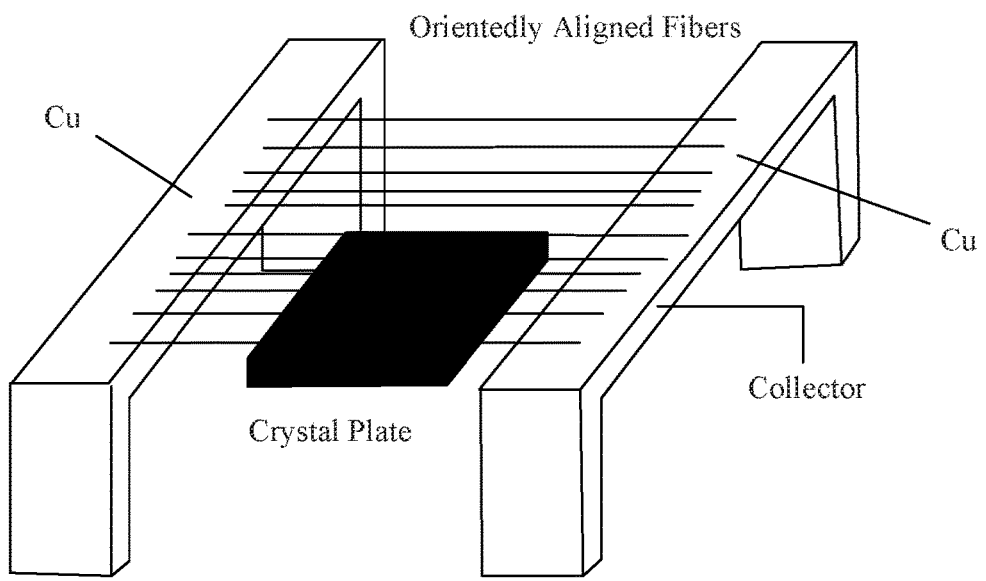
Figure 2B:
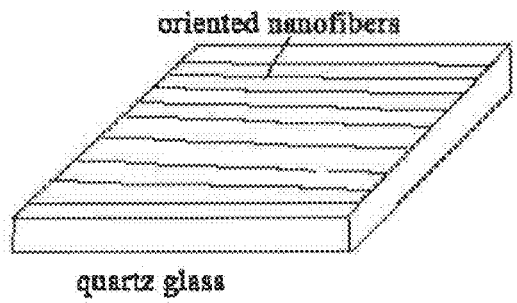
Figure 2C:
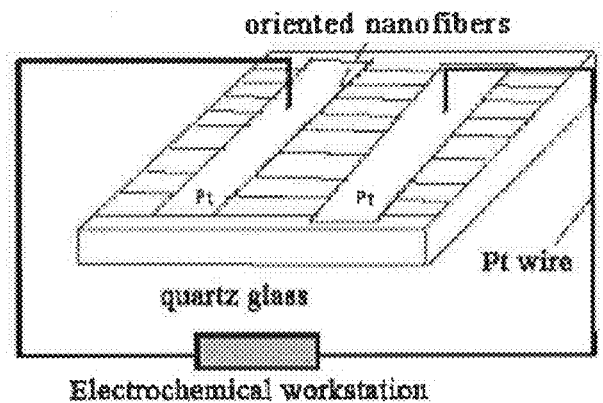
Figures 3A, 3B:
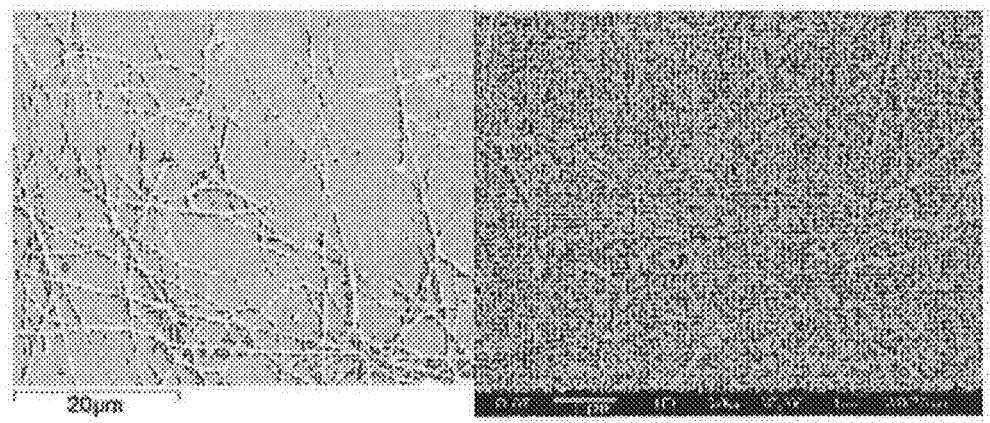
Figure 4:
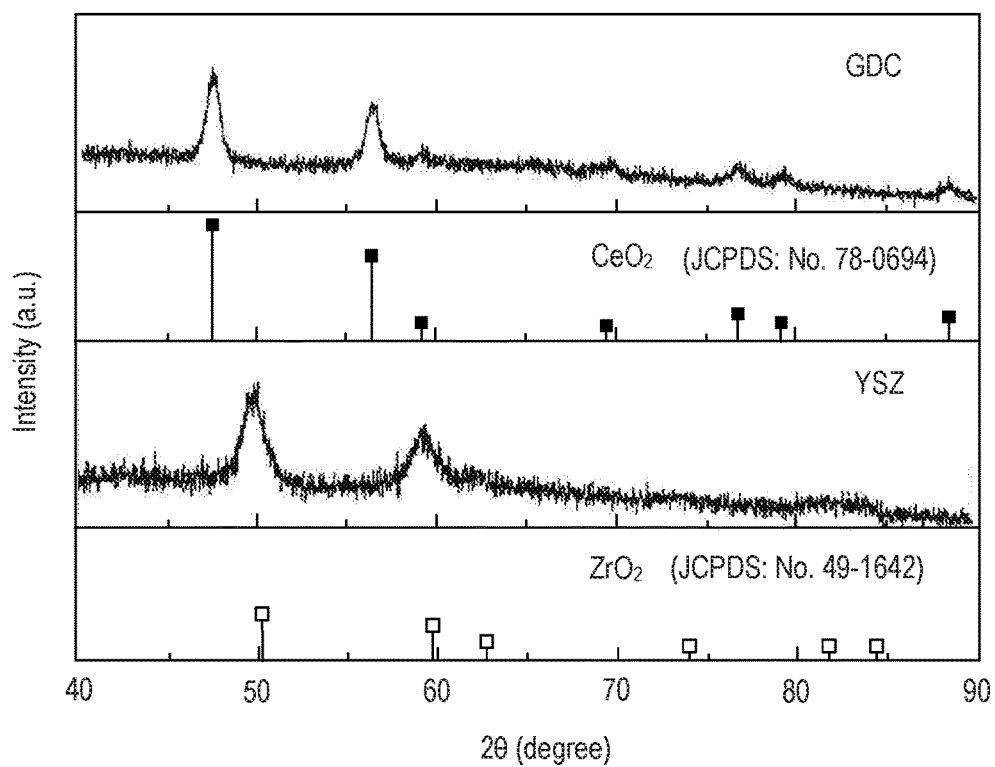
FIG. 4 shows the X-ray diffraction pattern of GDC and YSZ nanofibers prepared by the production method according to an Example of the present invention.
Figure 5A:
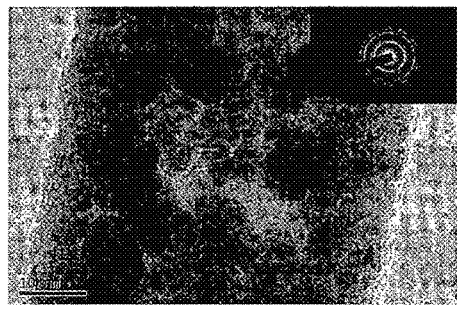
Figure 5B:
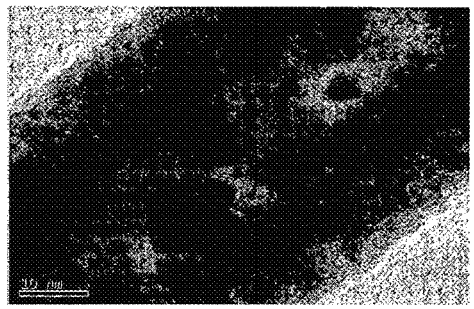
Figure 5C:
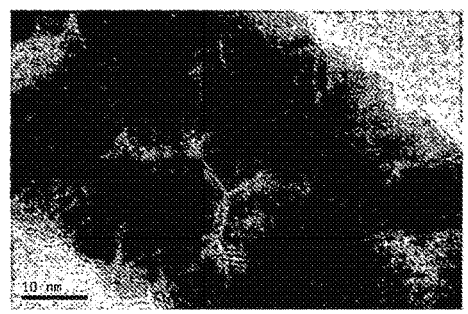

FIGS. 2(a), 2(b), and 2(c) are schematic diagrams of an apparatus specially designed for manufacturing precursor nanofibers in one-dimensional oriented alignment. The precursor nanofibers in one-dimensional oriented alignment can be obtained by using such apparatus for precursor nanofibers in one-dimensional oriented alignment, and further measurement of electrical properties of the calcined nanofibers can be conveniently carried out, and simultaneously solid electrolyte materials used for fuel cells or oxygen sensors can be conveniently prepared. As shown in FIG. 2(a), the cathode of the substrate for receiving the precursor nanofibers is composed of two grounded parallel copper plates of 1 cm in width with good conductivity. The precursor nanofibers containing the metal salt were spun under the effect of the electric field, and aligned in parallel between the two copper plate electrodes, and then directly transferred onto a quartz glass substrate of 1 mm in thick.

The resultant precursor nanofibers are subjected to calcining for 2 h under 500° C., 600° C. or 750° C., respectively, to give the nanofibers of metal oxide (FIG. 2(b)).

To ensure good electrical connections, two platinum electrodes of 70 μm apart were fabricated in a direction perpendicular to the metal oxide nanofibers in oriented alignment. The apparatus for testing conductivity properties was shown in FIG. 2(c). There were about 75 nanofibers on average between a pair of parallel electrodes.

Measurement of Electrical Properties of the Nanofibers

The AC Impedance Spectroscopy of the GDC and YSZ nanofibers in a temperature range of 400° C. to 650° C. was measured in the air atmosphere with an electrochemical workstation (Zahner, IM 6, Germany), and the intergranular, intragranular and total conductivity of the GDC and YSZ nanofibers were then calculated.

Figure 6:
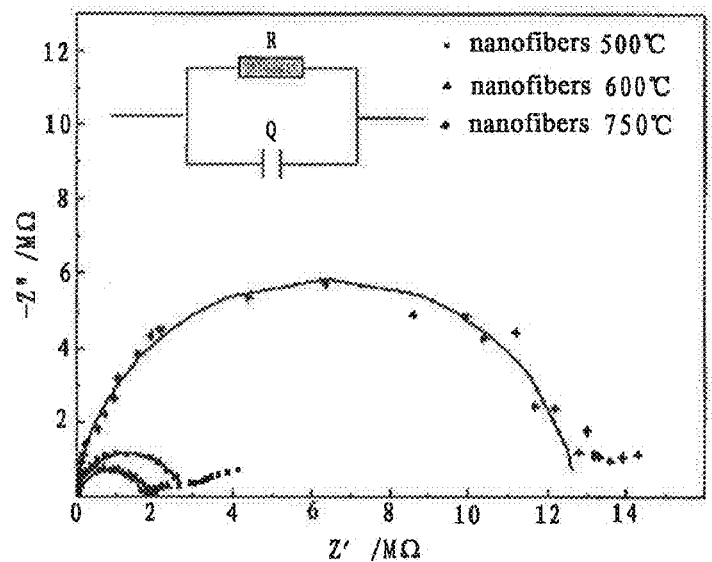
FIG. 6 shows an AC Impedance Spectroscopy measured in the air of the GDC nanofibers obtained by the production method according to an Example of the present invention by calcining under 500° C., 600° C. and 750° C., respectively.

FIG. 6 shows the test results for the AC Impedance Spectroscopy of the GDC nanofibers calcined under 500° C., 600° C. and 750° C. respectively, measured under 500° C. in the air. In case of a grain diameter less than 30 nm, the AC Impedance Spectroscopy curve consists of only a single arc, which is consistent with the results of most existing research reports.

The impedance values of the tested samples were obtained from the result of the AC Impedance Spectroscopy test curves by fitting according to the RQ equivalent circuit. R here represents resistance, whilst Q represents constant phase element, CPE. Then, the total impedance (intragranular+intergranular) was determined by the tangent of the semicircle on the real part axis. As shown in FIG. 6, as the calcining temperature for the metal oxide nanofibers increases from 500° C. to 750° C., the impedance value of the GDC sample firstly decreases and then increases. The sample calcined at 600° C. has the minimum value. Hence, the GDC nanofibers calcined at 600° C. have the highest conductivity.

The conductivities of the GDC and YSZ nanofibers can be calculated by the formula $4L/(n\pi Rd^2)$. Here, R represents the resistance of the nanofibers from the results of the AC Impedance Spectroscopy test, L represents the distance between the platinum electrodes on the nanofibers (L=70 μm), d represents the diameter of a nanofiber (d=50 nm), n represents the number of nanofibers (n=75).

FIG. 7 shows the conductivity data calculated as mentioned above. The conductivity properties of the already reported GDC and YSZ bulk ceramics (with average grain diameter of greater than 500 nm), are likewise listed in FIG. 7 for comparison. The conductivities of the GDC or YSZ nanofibers obtained under different calcining temperatures are much higher than the conductivities of the reported GDC or YSZ bulk ceramics. To be specific, the conductivity of the GDC nanofibers is 4.00 S/cm when measured at the temperature of 500° C., whilst it is 0.01 S/cm when measured at the temperature of 210° C. The properties of the nanofibers are much better than those of the bulk materials with the same composition reported before.

Although the specific mode for carrying out the present invention has been described in details by referring to various exemplary embodiments of the present invention, it should be understood that a person skilled in the art can design many other modifications and embodiments which fall within the spirit and range of the principle of the present invention. To be specific, reasonable modifications and improvements made based on conventional techniques within the range of the former disclosure, the figures and the claims will not deviate from the spirit of the present invention. The scope of the present invention is restricted by the attached claims and equivalents thereof.

The invention claimed is:

1. A method for producing an oxygen sensor, the method comprising:
    spinning a compound precursor consisting of a salt of at least one metal selected from Sc, Y, La, Ce, Pr, Nd, Sm, Gd, Dy, Ho, Yb, Sr, Ba, Mn, Co, Mg and Ga, a solvent, and a macromolecular polymer to produce nanofibers of the compound precursor containing the salt of the metal, wherein an average molecular weight of the macromolecular polymer ranges from 1,000 to 100,000;
    calcining the nanofibers of the compound precursor containing the salt of the metal at a temperature ranging from 550° C. to 650° C. for 2 to 4 hours, to obtain nanofibers of metal oxide containing the at least one metal,
    making a solid electrolyte material composed of the nanofibers obtained from the calcining, and
    producing a part of the oxygen sensor from the solid electrolyte material.

2. The method according to claim 1, wherein the metal oxide is a metal oxide of at least one metal chosen from Sc, Y, La, Ce, Pr, Nd, Sm, and Gd.

3. The method according to claim 1, wherein the nanofibers of the compound precursor containing the salt of the metal are prepared by electrospinning or liquid phase spinning method.

4. The method according to claim 1, wherein the metal oxide is a metal oxide of at least two metal elements chosen from Sc, Y, La, Ce, Pr, Nd, Sm, Gd, Dy, Ho, Yb, Sr, Ba, Mn, Co, Mg and Ga.

5. The method according to claim 1, wherein a concentration of the macromolecular polymer is 5 mass % to 15 mass % with respect to a total mass of the compound precursor.

6. The method according to claim 1, wherein the nanofibers of metal oxide are composed of metal oxide crystal with a three-dimensional structure, and in the nanofibers of metal oxide, adjacent metal oxide crystal grains connect to have a grain boundary network structure.

* * * * *